(12) United States Patent
Riva

(10) Patent No.: US 9,872,695 B2
(45) Date of Patent: *Jan. 23, 2018

(54) DEVICE FOR TREATMENTS OF ENDOSCOPIC RESECTION/ REMOVAL OF TISSUES

(71) Applicant: FRII SA, Luxembourg (CH)

(72) Inventor: Raffaele Riva, Lugano (CH)

(73) Assignee: FRII SA, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 14/132,629

(22) Filed: Dec. 18, 2013

(65) Prior Publication Data
US 2014/0171998 A1 Jun. 19, 2014

(30) Foreign Application Priority Data
Dec. 19, 2012 (CH) ...................... 2861/12

(51) Int. Cl.
*A61B 17/14* (2006.01)
*A61B 17/32* (2006.01)
(Continued)

(52) U.S. Cl.
CPC ............ *A61B 17/32002* (2013.01); *A61B 2017/00455* (2013.01); *A61B 2017/00477* (2013.01);
(Continued)

(58) Field of Classification Search
CPC ........ A61B 17/32; A61B 2017/320016; A61B 2017/32002; A61B 2017/320028;
(Continued)

(56) References Cited

U.S. PATENT DOCUMENTS 3,452,741 A 7/1969 Schaffer
3,797,497 A * 3/1974 Crim .................. A61B 17/1617
606/173
(Continued)

FOREIGN PATENT DOCUMENTS

DE 102006033439 A1 1/2008
EP 0700663 A2 3/1996
(Continued)

OTHER PUBLICATIONS

End. (n.d.). Dictionary.com Unabridged. Retrieved Mar. 7, 2016 from Dictionary.com website http://dictionary.reference.com/browse/end.*
(Continued)

*Primary Examiner* — Katrina Stransky
*Assistant Examiner* — Kankindi Rwego

(57) ABSTRACT

Device for treatments of endoscopic resection/removal of tissues including: a handpiece; an outer tubular element extending along a longitudinal axis including a proximal end, a distal end and a cutting opening at the distal end; an inner tubular element rotatably accommodated in the outer tubular element; the inner tubular element extending along a longitudinal axis and including a proximal end, a distal end and a cutting tip at its distal end; a guide for rotating/oscillating the inner/outer tubular elements with respect to one another; the guide including an electric motor and power-supply; a first clutch keyed on the inner tubular element substantially at the proximal end of the inner tubular element; a second clutch keyed on the distal end of the motor output shaft to axially slide on the motor output shaft; and at least one elastic element to push the second clutch to couple with the first clutch.

24 Claims, 4 Drawing Sheets

(51) Int. Cl.
  *A61B 17/00* (2006.01)
  *A61B 90/00* (2016.01)
(52) U.S. Cl.
  CPC ............... *A61B 2017/00482* (2013.01); *A61B 2017/00734* (2013.01); *A61B 2090/0813* (2016.02)
(58) Field of Classification Search
  CPC ....... A61B 2017/320032; A61B 2017/320052; A61B 2017/320053; A61B 2017/320758; A61B 17/32002; A61B 17/3205; A61B 17/3207; A61B 17/320783; A61B 17/320785; A61B 2017/2903; A61B 2017/2912; A61B 2017/2913; A61B 2017/2916; A61B 2017/2948; A61B 2017/32008; A61B 2017/32004; A61B 2017/320766; A61B 2017/320775; A61B 2017/320791; A61B 10/02; A61B 10/0233; A61B 10/0241; A61B 10/025; A61B 10/0266; A61B 10/0275; A61B 10/0283; A61B 10/0291; A61B 10/04; A61B 10/06; A61B 2010/0208; A61B 2010/0216; A61B 2010/0225; A61B 2010/0258; A61B 2010/045
  See application file for complete search history.

(56) References Cited

U.S. PATENT DOCUMENTS

| | | |
|---|---|---|
| 3,995,619 A | 12/1976 | Glatzer |
| 4,050,528 A | 9/1977 | Foltz et al. |
| 4,217,964 A | 8/1980 | Eaton |
| 4,649,919 A | 3/1987 | Thimsen et al. |
| 4,867,155 A | 9/1989 | Isaacson |
| 5,163,433 A | 11/1992 | Kagawa et al. |
| 5,372,602 A | 12/1994 | Burke |
| 5,376,089 A | 12/1994 | Smith |
| 5,490,860 A * | 2/1996 | Middle ............ A61B 17/32002 604/22 |
| 5,492,527 A | 2/1996 | Glowa et al. |
| 5,505,210 A | 4/1996 | Clement |
| 5,669,921 A | 9/1997 | Berman et al. |
| 5,759,185 A | 6/1998 | Grinberg |
| 5,796,188 A | 8/1998 | Bays |
| 5,810,809 A | 9/1998 | Rydell |
| 5,849,023 A | 12/1998 | Mericle |
| 5,893,858 A | 4/1999 | Spitz |
| 6,152,941 A | 11/2000 | Himes et al. |
| 2003/0163134 A1 | 8/2003 | Riedel et al. |
| 2003/0181934 A1 | 9/2003 | Johnston et al. |
| 2004/0073195 A1 | 4/2004 | Cucin |
| 2004/0092992 A1 | 5/2004 | Adams et al. |
| 2005/0159752 A1 | 7/2005 | Walker et al. |
| 2007/0010823 A1 | 1/2007 | Kucklick |
| 2008/0208233 A1 | 8/2008 | Barnes et al. |
| 2008/0234715 A1 | 9/2008 | Pesce et al. |
| 2014/0155925 A1 * | 6/2014 | Riva ................ A61B 17/32002 606/171 |

FOREIGN PATENT DOCUMENTS

| | | |
|---|---|---|
| GB | 2087239 A | 5/1982 |
| WO | WO96/29014 | 9/1996 |
| WO | 09632894 | 10/1996 |
| WO | WO99/13790 | 3/1999 |
| WO | WO03/079911 A1 | 10/2003 |
| WO | 2004028351 | 4/2004 |
| WO | 2008011308 | 1/2008 |
| WO | 2010/146432 | 6/2010 |
| WO | WO2016/176304 A1 | 11/2016 |

OTHER PUBLICATIONS

Search Report of application CH00941/09 dated Aug. 28, 2009.

* cited by examiner

DEVICE FOR TREATMENTS OF ENDOSCOPIC RESECTION/ REMOVAL OF TISSUES

FIELD OF THE INVENTION

The present invention concerns a device for treatments of endoscopic resection/removal of tissues. In particular, the invention refers to an endoscopic device for resection treatments of soft tissue and bone tissue (with the respective removal of splinters made in such an action).

KNOWN ART

In alternative to conventional surgery, requiring a relatively large incision for accessing to surgical site inside the human body, the endoscopic procedures use natural accesses or, alternatively, the creation of little portals (minimum tissue incisions); therefore, it is often referred to the endoscopic surgery with the term mini-invasive surgery. Two prime advantages of the endoscopic surgery are the more rapid healing of tissues after the operation and the less exposure of inner tissues to infection risks. Technology developments in this surgery field, also defined as "closed surgery", led to the implementation of a number of minimally invasive instruments: that's because the access to surgical site happens through one or more portals. Such instruments must be sufficiently elongated and smooth to allow the entrance and use thereof with a minimum trauma for the surrounding tissues. An instrument portion, usually referred as "distal portion", is designed for the access to the surgical site; the opposite portion, usually referred as "proximal portion", remains outside of the patient body. The distal portion of the instrument is typically designed for treating the tissue it will come in contact with, therefore its shape and size are specifically designed for the particular surgical operation it is intended for.

The proximal portion, on the contrary, is provided with a mechanism for controlling the afore said function from the outside of the patient body. The motorized endoscopic surgical instruments, used in the "closed" surgery, often referred as "endoscopic shaver", are typically composed of a couple of coaxial, concentrically arranged, tubular elements: an outer element that ends distally with an opening or "cutting window" and a rotating inner element having a cutting surface at the cutting window. The rotation action of the inner tubular element causes the tissue removing or finishing by abrasion, this process being defined as "resection".

As in any surgical action, also in endoscopic surgery there is the presence of two well defined fields: the sterile field, that in close contact with the patient, where the surgeon will exercise the action, and that clearly separated from the patient and from every object coming in contact therewith. In the sterile field only personnel and instruments properly treated can access (sterilizing processes for instruments, pre-operation washing processes and adoption of protection guards for the personnel, such as gloves and whitecoats); all that cannot come in contact with the sterile field must strictly remain outside of it.

The Applicant observed that, in currently existing endoscopic shaver and/or in those afore described, the inner tubular element is rotated and controlled by a handpiece having in its inside a little electric motor; activation and control happen either by buttons placed on the hang grip itself or by buttons placed on pedals. In both cases, the power and the control signal come to the handpiece through a cable connected to an outer console. This "console" is usually positioned on a trolley sufficiently distant from the operation field in order to not infect the sterile field. The handpiece (contacting the sterile field) undergoes a sterilization treatment before every surgical operation; the console, having to stay out of contact with the sterile area, is housed outside the afore said field; in currently existing systems, a connecting cable is provided between the hang grip and the "console". Before every use, such a connecting cable is treated to become completely sterile and, when the surgical operation is prepared, it is assembled with the handpiece (sterile) at one end and, at the other end, with the console (not sterile).

At the end of every operation, the personnel of the surgical room taking care of the instrument treatment and handling has to wash (through appropriate disinfectants and detergents) and after to sterilize the re-sterilizable parts (handpiece and cable); cleanliness and sterilization affect negatively on the lifetime of sterilizable components.

The room personnel have further to provide for the stocking in appropriate containers assuring the sterility, with the consequent time and space usage.

Nevertheless, the personnel of the surgical room have to take it upon itself to maintain non-sterilizable components, i.e. the console and in case the pedals, by planning periodical inspections that could require more complex technical services by the skilled personnel.

To solve the afore stated problems, in the Application WO2010/146432 in the name of the same Applicant, a device for treatments of endoscopic resection/removal of tissues has been proposed, providing an essential disposable portion of the device. Such a portion is represented by the handpiece containing the motor and the power system that are mounted to form a body integral and removable with respect to the handpiece itself. In this way, the most expensive portion of the device, i.e. the motor, is reclaimed.

However, the Applicant observed that for the afore described device type, in some cases during the surgical operation itself, it is necessary that the surgeon could change the outer and inner tubular elements, in order to carry out some steps of the operation without necessarily changing the whole handpiece.

This alternative, with respect to that afore described, allows an additional decrease of costs where the user would have the need of tubular members with different cutting edges.

However, the Applicant observed that making the outer/inner tubular element assembly interchangeable with another, and then disposable, involves big problems in terms of alignment of motor axis/rotation axis of inner/outer tubular element, coupling of parts and sealing.

In addition, the Applicant found the need of a clutch between the blade shank (inner tubular element shank) and the motor shaft that assures a simple and accurate coupling between the two parts.

In addition, the Applicant noticed that, in particular for such a described device, it is preferred that the motor and specifically its output shaft do not need marks for operatively coupling with the blade shank, in order to obtain a better constructive easiness.

SUMMARY OF THE INVENTION

The Applicant found that with a device for treatments of endoscopic resection/removal of tissues providing a first clutch keyed on the inner tubular element, a second clutch keyed on the distal end of the motor output shaft and a transmitting member interposed between precedents, it is possible to obtain a simple and accurate operative coupling of the two clutches and, in addition, differently from the existing devices, the motor and particularly its output shaft, do not need of marks for coupling with the blade shank.

In its first aspect, the present invention concerns a device for treatments of endoscopic resection/removal of tissues comprising:

a handpiece adapted to be grasped by an user;
an outer tubular element extending along a longitudinal axis (X-X) comprising a proximal end, a distal end and a cutting opening arranged at said distal end;
an inner tubular element adapted to be rotatably accommodated in said outer tubular element; said inner tubular element extending along a longitudinal axis (X-X) and comprising a proximal end, a distal end and a cutting tip at its distal end;
guiding means for rotating and/or oscillating said inner tubular element with respect to said outer tubular element; said guiding means comprising an electric motor and at least one power-supply battery pack for said electric motor contained inside said handpiece;
characterized by comprising:
a first clutch keyed on the inner tubular element substantially at the proximal end of the inner tubular element to make rotate said inner tubular element;
a second clutch keyed on the distal end of the motor output shaft so that to axially slide on the motor output shaft;
a motion transmitting member, interposed between said first clutch and said second clutch for decoupling the first clutch from said second clutch;
said transmitting member being shaped to couple with said second clutch and said first clutch;
and said first clutch being shaped for removably coupling with said transmitting member.

The present invention, in the afore said aspect, may present at least one of the preferred characteristics herein after described.

Conveniently, the transmitting member comprises:
a third clutch adapted for coupling with said first clutch;
a fourth clutch adapted for coupling with said second clutch; and
at least one sealing element extending radially in order to avoid the fluid passage to said guiding means.

Preferably, the first clutch comprises a first crown wheel comprising a plurality of teeth spaced along a circumference to form a plurality of seats and in that said third clutch comprises a third crown wheel comprising a plurality of teeth spaced along a circumference to form a plurality of seats.

Advantageously, the second clutch comprises a second crown wheel comprising a plurality of teeth spaced along a circumference and adapted to form a plurality of seats of the second crown wheel and said third clutch comprises a fourth crown wheel comprising a plurality of teeth spaced along a circumference to form a plurality of seats of the fourth crown wheel.

Preferably, the transmitting member further comprises at least one centering element radially extending around a longitudinal axis X-X to axially align said first clutch with the third clutch and the second clutch with said fourth clutch.

Advantageously, the transmitting member comprises a fastening element to radially constrain the transmitting member to the handpiece.

Preferably, the third clutch and the fourth clutch are disjointly made and comprise removable fastening means to make them integral.

Advantageously, the transmitting member comprises an abutment element for the sealing element comprising a disc-shaped element that radially extends around the central axis X-X from the second clutch.

Conveniently, the device for treatments of endoscopic resection/removal of tissues comprises a supporting element fixedly-keyed through fastening means to the motor output shaft; the supporting element being adapted to make rotate the second clutch.

The device for treatments of endoscopic resection/removal of tissues comprises at least one elastic element to push the second clutch to couple with the fourth clutch and the third clutch to couple with the first clutch.

Advantageously, the elastic means comprise a spring concentrically mounted on the motor output shaft and interposed between said second clutch and said supporting element to apply a thrust longitudinally onto said second clutch.

Preferably, the device comprises a limit element of the longitudinal sliding of said second clutch, said limit element being mounted on the end of said motor output shaft, distally from said second clutch.

Conveniently, the electric motor and said at least one power-supply battery pack are contained in at least one closed body, in its turn removably contained in the handpiece.

Preferably, the handpiece is disposable.

BRIEF DESCRIPTION OF THE DRAWINGS

Further characteristics and advantages of the invention will be more evident from the detailed description of some preferred embodiments, but not exclusive, of a device for treatments of endoscopic resection/removal of tissues according to the present invention.

Such a description will be hereinafter explained referring to the attached drawings, provided for purposes of illustrations only, and thereby not limitative, wherein:

FIG. 2*a* is a perspective schematic view of the inner and outer tubular elements assembled according to the present invention;

DETAILED DESCRIPTION OF SOME EMBODIMENTS OF THE INVENTION

Figure 1:
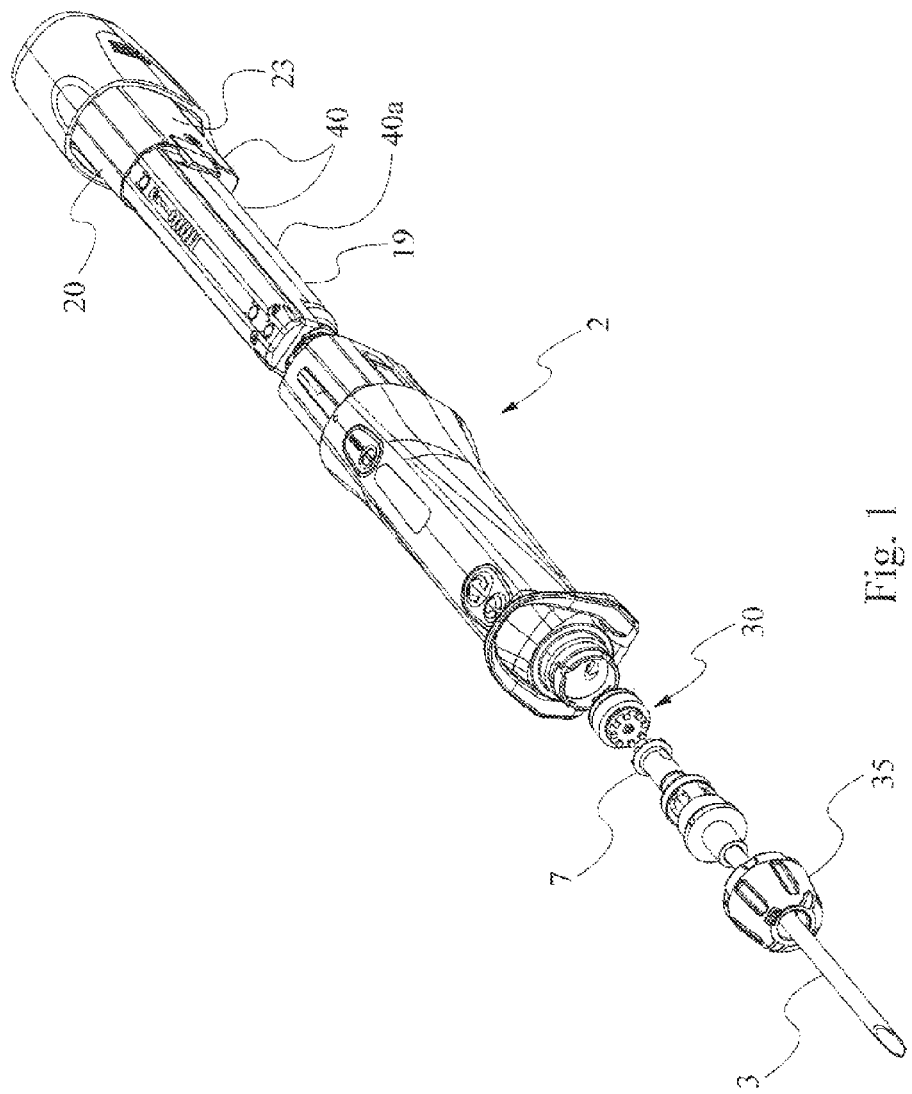
FIG. 1 is a schematic exploded view of a preferred embodiment of the device for treatments of endoscopic resection/removal of tissues according to the present invention.

Referring to FIGS. 1-4, the device for treatments of endoscopic resection/removal of tissues is indicated with numeral 1.

The device 1 for treatments of endoscopic resection/removal of tissues comprises a handpiece 2 adapted to be grasped by an user, an outer tubular element 3, an inner tubular element 4 and guiding means 5 to make rotate and/or oscillate the inner tubular element 4 with respect to the outer tubular element 3.

The outer tubular element 3 extends along a longitudinal axis X-X and comprises a proximal end, a distal end and a cutting opening and/or window arranged at the distal end.

The inner tubular element 4 is shaped and sized to be rotatably accommodated in the outer tubular element 3 and it extends too along the longitudinal axis X-X. The inner tubular element 4 comprises a proximal end, a distal end and a cutting tip at its distal end, to face towards the cutting window. The rotation action of the inner tubular element 4 causes the tissue removing or finishing by abrasion, this process being defined as "resection".

The guiding means 5 comprises an electric motor 19 and a power-supply battery pack 20 for the electric motor 19. In a preferred embodiment, the guiding means 5 can be reusable, whereas the handpiece and the assembly made of the outer 3 and inner 4 tubular elements are disposable or single-use. For this purpose, the guiding means 19 are contained inside an appropriate body 40 completely housable inside the handpiece 2. The body 40 is contained and removably fastened inside the handpiece 2. In this way, the most expensive portion of the device is reclaimed.

To allow a simple and quick drawing out of the guiding means 5 and in particular of the body 40 with respect to the handpiece 2, the handpiece 2 can comprise a distal portion 2a supporting, as explained more in detail hereinafter, the outer tubular element 3 and the inner tubular element 4 and a proximal portion 2b removably couplable to the distal portion 2a.

The electric motor 19 is preferably a brushless type motor, but another type of electric motor of appropriate size and equal power can be suitable. The motor 19 is able to rotate at a speed comprised between 400 and 6000 rpm.

The electric motor 19 is driven by a controlling unit that control all functions of the device 1, i.e. the power-on, the rotation or the simple oscillation of the inner tubular element 4 with respect to the outer tubular element 3, and the rotation speed of the inner tubular element 4.

The controlling unit is provided in the body 40 too.

The controlling unit comprises at least one main electronic circuit supported by a supporting electronic circuit and an auxiliary electronic circuit.

The main electronic circuit is connected to push-button controls that allow selecting the instruction type to be sent to the main electronic circuit from the outside, i.e. the switching on or off of the device 1, the type of oscillation/rotation function of the inner tubular element.

The power-supply battery pack 20 of the preferred embodiment shown in FIGS. 1-4 is represented by alkaline or lithium rechargeable batteries, but every other battery type can be properly used without departing from the protection scope of the present.

The batteries are contained inside a container 23 provided at the most proximal end of the body 40a.

In other terms, in this embodiment there are at least two bodies, one 40a specifically for the electric motor 19 and one 23 for the battery pack 20.

The container 23 has the electrical connections adapted to supply the electric motor 19 and a removable lid for the replacement of batteries and to inspect the electrical connections.

Preferably, the container 23 is sealed too.

The electric motor 19 is housed in the body 40a extending axially inside the handpiece 2.

The body 40a contains the driving pinion centrally, in a position proximal to the controlling unit that drives and controls the motor 19 and, frontally, the motion transmitting assembly.

As visible in FIG. 1, the outer tubular element 3, through a blocking ring nut 35 is associated with the handpiece 2, and in particular with the distal portion 2a.

The blocking ring nut 35 removably fastens the outer tubular element 3 to the handpiece 2 and, consequently, also the inner tubular element 4.

In use, the inner 4 and outer 3 tubular elements are assembled together and removably constrained to said handpiece 2 through the blocking ring nut 35, provided with an appropriate thread 70 adapted to engage in a reverse thread 71 provided on the handpiece 2.

Further, inside the body 40a there is a motion transmitting assembly, comprising satellite gears.

In detail, the inner tubular element 4 is carried by a motor output shaft 17 that operatively connects, through a driving pinion, the inner tubular element with the electric motor 19.

In addition, the box of the satellite gears is provided between the driving pinion and the motor output shaft 17, comprising the satellites and the shaft supporting the satellites.

The motion transmitting assembly further provides two radial bearings radially interposed between the motor output shaft 17 and the box of the satellite gears.

The driving pinion meshes the satellites that transfer the motion to the motor output shaft 17 through the shaft supporting the satellites.

Alternatively, a gear-train transmission assembly can be provided to the just described coaxial transmitting assembly, always providing the output shaft 17 operatively connected to the electric motor 19 through the driving pinion.

However in this case, between the driving pinion and the output shaft 17, first reduction pinions, a pivot pin of the first reduction pinions and shim washers can be provided.

The motor output shaft 17 can be rotatably supported by a bearing or brass arranged at the end axially distal from the motor output shaft 17.

According to an important aspect of the present invention, the device 1 comprises a first clutch 7 that, as can be seen hereinafter, is associated with the inner tubular element 4, a second clutch 8 keyed on the distal end 17b of the motor output shaft 17 so that to axially slide on the motor output shaft 17 and a transmitting member 30 interposed between the first 7 and the second 8 clutch in order to transmit the movement of the motor output shaft 17 to the inner tubular element 3.

In other terms, the second clutch 8 is operatively coupled with the first clutch 7 through the transmitting member 30 in order to make rotate the inner tubular element 4.

Figure 4:
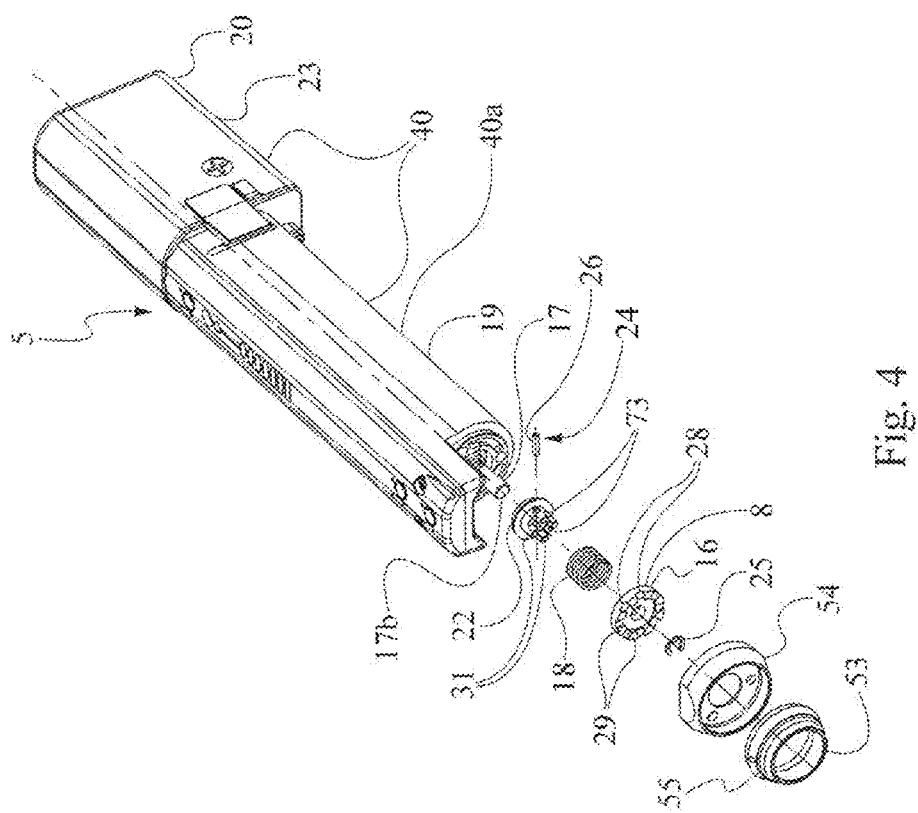
FIG. 4 is a schematic exploded view of the proximal portion of the device of FIG. 1.

In addition, as shown in particular in FIG. 4, there is at least one elastic element 18 to push the second clutch 8 to operatively couple with the first clutch 7 through the transmitting member 30.

Figure 2:
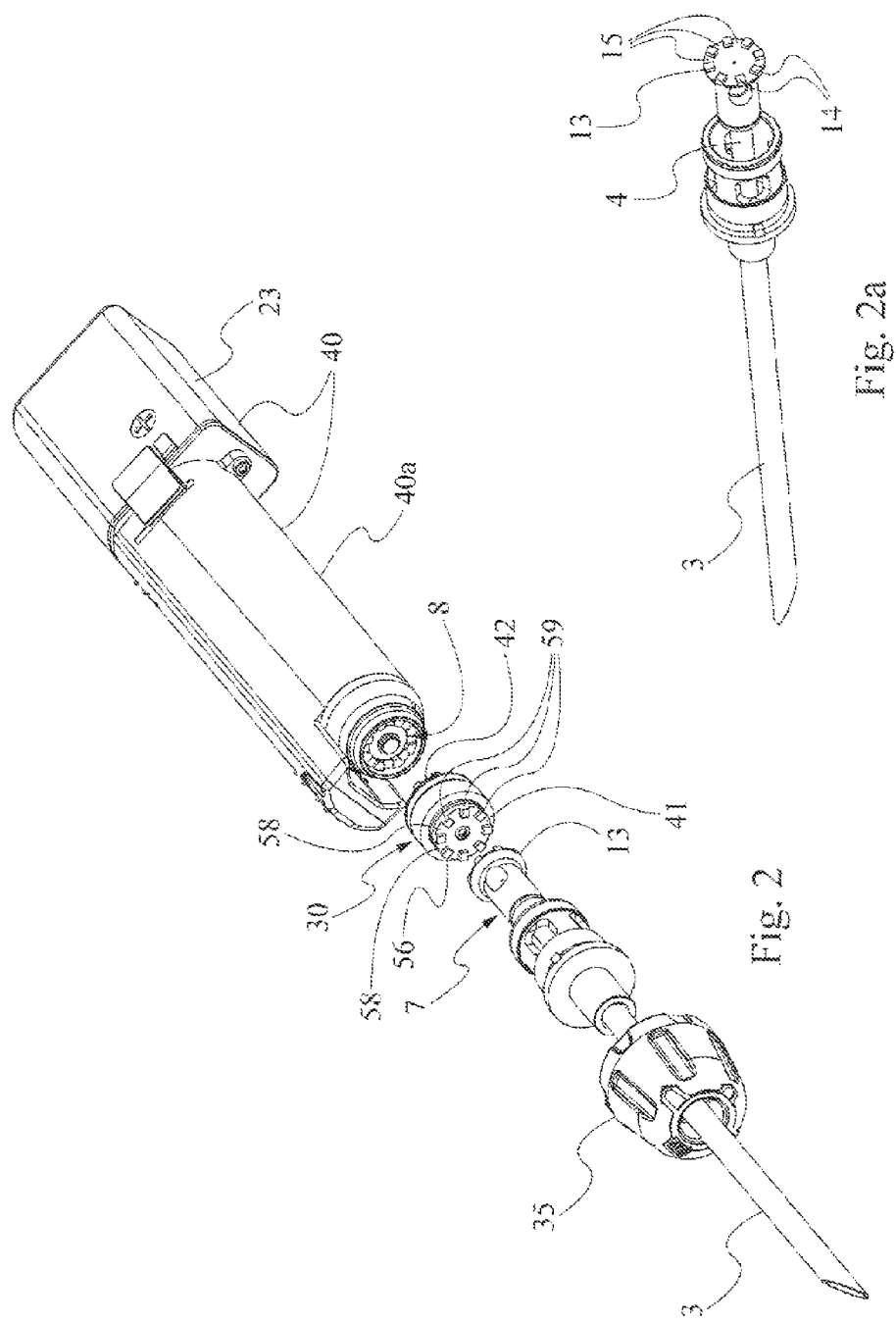
FIG. 2 is a schematic exploded view of the distal portion of the device of FIG. 1.
Figure 3:
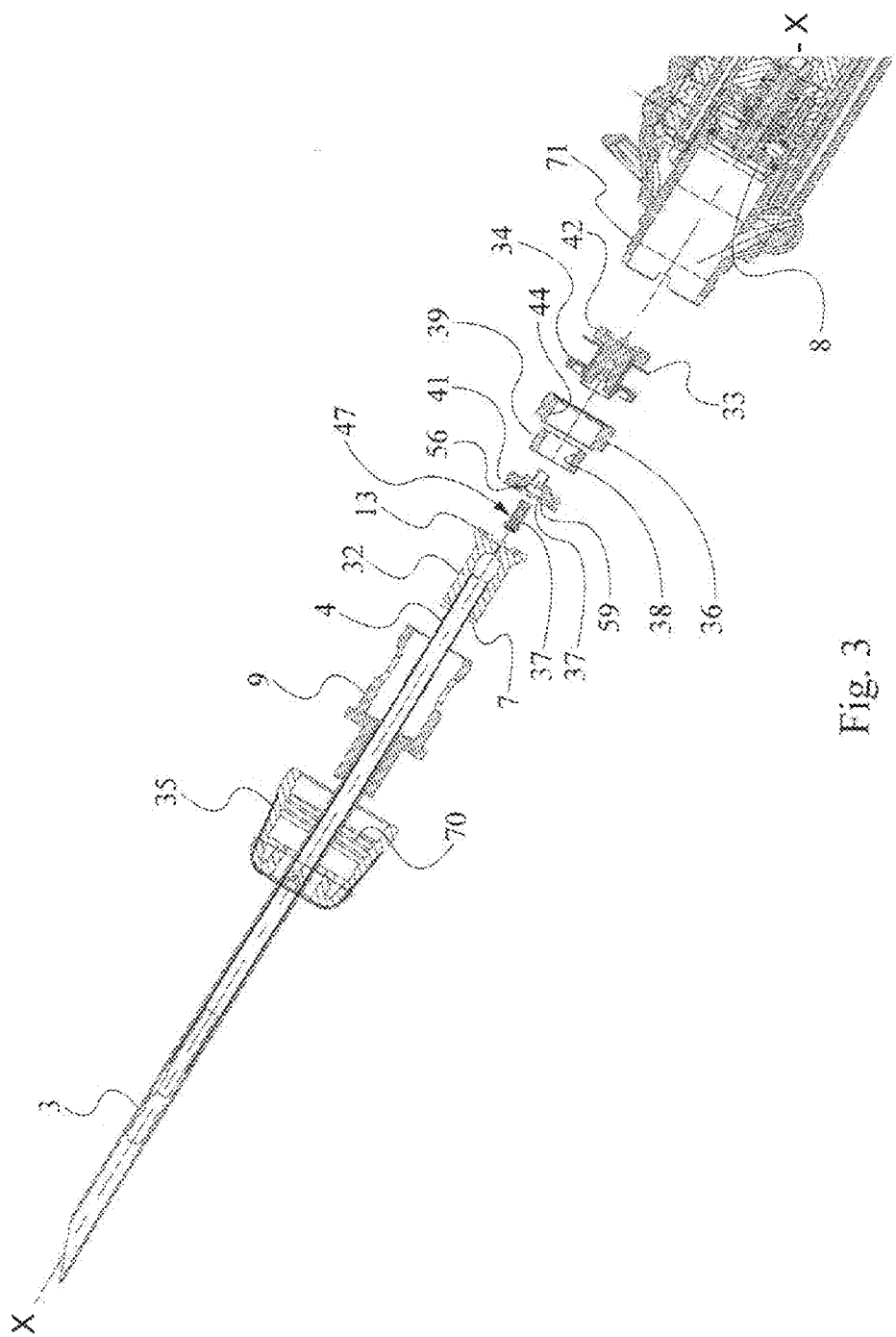
FIG. 3 is another schematic exploded view of a inner portion of the device for treatments of endoscopic resection/removal of tissues shown in FIG. 1.

In particular, in the embodiment shown in FIGS. 2 and 3, the first clutch 7 has a first crown wheel 13 comprising a plurality of teeth 14 spaced along a circumference to form a plurality of seats 15 of the first crown wheel 13.

Preferably, as in the embodiment shown in figures, there are eight seats 15 and eight interspaced teeth 14.

The first crown wheel 13 is made of plastic and is fixedly hot keyed on the inner tubular element 4.

The first clutch 7 further provides a bushing 32 supporting the first crown wheel 13 at one end.

In the embodiment shown in figures, the transmitting member 30 has a third 41 and a fourth 42 clutches that extend radially around an axis Y-Y and are axially opposed so that the third clutch 41 can be coupled with the first clutch 7 and the fourth clutch 42 can be coupled with the second clutch 8.

The transmitting member 30, by coupling de facto, i.e. operatively, the motor output shaft 17 with the inner tubular element 4, allows the former to make rotate the latter thereby assuring the motion transmission from the motor to the inner tubular element 4.

The first clutch 7 is removably mounted on the third clutch 41, thereby making removable, and then disposable, the first clutch 7 with the inner tubular element 4 associated thereto and the outer tubular element.

Advantageously, the transmitting member 30 operatively couples the motor output shaft 17 with the inner tubular element 4 so that there is a substantially axial alignment between the motor output shaft 17 and the inner tubular element 4.

Preferably, an axial alignment along the axis X-X.

On the outer tubular element 3, as better shown in FIG. 3, there is an outer guiding element 9 made preferably of plastic, adapted to coupled with, and to be concentrically mounted on, the bushing 32.

The outer guiding element 9 is fixedly keyed, preferably hot keyed, on the outer tubular element 3.

In this way, the ring nut 35 coupled to the handpiece 2 through the threads 70, 71 and the removable coupling between the first clutch 7 and the third clutch 41 represent the only means for removably constraining the inner 4 and outer 3 tubular elements 3 to the handpiece 2.

The afore said arrangement and shape of parts and the presence of the transmitting member 30 allows making removable, and consequently disposable, the inner 4 and outer 3 tubular elements, solving the sterilization, storage and reuse problems of most expensive parts of the device typical of the known art.

Similarly to the first clutch 7, the third clutch 41 of the transmitting member 30 comprises a third crown wheel 56 that has a plurality of teeth 59 too, which are spaced along a circumference and shaped and sized so as to engage with the seats of the first crown wheel 13 present on the first clutch 7.

The teeth 59 of the third crown wheel 56 are in turn spaced along a circumference so that to form a plurality of seats 58 adapted to accommodate in engagement the teeth of the first crown wheel 13.

Preferably, as in the embodiment shown in figures, there are eight seats 58 and eight interspaced teeth 59.

The second clutch 8 comprises a second crown wheel 16 that has a plurality of teeth 29 too, which are spaced along a circumference and shaped and sized so as to engage with the seats of a fourth crown wheel present on the transmitting member 30.

In particular, the fourth clutch 42 has a fourth crown wheel comprising a plurality of teeth circumferentially spaced with respect to a plurality of seats, not clearly shown in figures.

The teeth 29 of the second crown wheel of the second clutch 8 are in turn spaced along a circumference so that to form a plurality of seats 28 adapted to accommodate in engagement the teeth of the fourth crown wheel.

Preferably, as in the embodiment shown in figures, there are eight seats 28 and eight interspaced teeth 29 for the second crown wheel 13.

In the embodiment shown in figure, the third clutch 41 and the fourth clutch 42 are made as two disjointed bodies and comprise removable fastening means to make them integral.

Preferably, the fastening means are represented by a male element projecting from the third clutch 41 adapted to enter into a hollow female element present on the fourth clutch 42.

The male and female elements, not numbered in figures, become integral by the screw 37.

Advantageously, the transmitting member 30 comprises a fastening element 36 to radially constrain the transmitting member 30 to the handpiece 2.

The fastening element 36 is in the shape of a cylindrical body provided with a central recess 44 for accommodating the third 41 and the fourth 42 clutches, when assembled, and an outer circumferential side surface adapted to face towards, and to engage with, an inner recess of the handpiece 2 housing the transmitting member 30.

Preferably, the transmitting member 30 further comprises at least one centering element 39 radially extending around the longitudinal axis X-X to axially align said first clutch 7 with the third clutch 41 and the second clutch 8 with said fourth clutch 42.

The centering element 39, in the embodiment shown in figure, is a cylindrical bushing interposed between the third 41 and the fourth 42 clutches, when assembled, and the fastening element 36.

In detail, the centering element 39 is housed in the central recess 44 and in its turn comprises a central recess 38 accommodating the third 41 and the fourth 42 clutches, when assembled.

To protect the guiding means 5, i.e. the electric motor 19 and the power-supply 20 mounted in the body 40, from the contamination of sucked liquids, the transmitting member 30 has a frontal sealing element 34.

In fact, the frontal sealing element 34 avoids the sucked liquids passing inside the inner tubular element 4 from contacting the body 40 and the guiding means 5 contained therein.

The frontal sealing element 34, in the embodiment shown in figures, is a disc-shaped element keyed on the fourth clutches 42 extending in the radial direction around the axis X-X up to meet the radially inner surface of the handpiece recess adapted to house the transmitting member 30 itself.

Preferably, the frontal sealing element 34 is made of PTFE, but it can be made of different materials without departing from the protection scope of the present invention.

Advantageously, the transmitting member 30 comprises an abutment element 32 for the frontal sealing element 34.

The abutment element 32 avoids deformations in radial directions of the frontal sealing element 34 and, in the embodiment shown in figures, comprises a disc-shaped element radially extending around the central axis X-X from the second clutch 42, substantially for the whole radial extension of the frontal sealing element 34.

Preferably, the abutment element 32 is in the shape of a stainless steel washer.

Referring to the embodiment shown in FIG. 4, upstream the second clutch 8 in the longitudinal direction, identified by the axis X-X, there is a supporting element 22 fixedly keyed to the motor output shaft 17.

The supporting element 22 is adapted to make rotate the second clutch 8 and it is fastened to the motor output shaft 17 through convenient fastening means 24, such as for example a grub screw 26 adapted to enter into an appropriate seat obtained on the motor output shaft 17.

To make rotate the second clutch 8, the supporting element 22 has four front teeth 31 circumferentially spaced so that to form four seats 33 adapted to couple with four teeth, not shown in figure, provided for such a purpose on the second clutch 8 and facing towards the supporting element 22.

In fact, the second clutch 8 has four little teeth circumferentially spaced to form as much seats, the latter not being shown in figure too. The little teeth are adapted to couple with the seats 73 of the supporting element 22 whereas the four seats of the second clutch 8 are sized and shaped to couple with the four frontal teeth 31 of the supporting element 22. When the device 1 is assembled and mounted, the four frontal teeth 31, respectively the four seats 73 of the supporting element 22, are engaged with the corresponding seats, namely little teeth, of the second clutch 8. Such a coupling is substantially free of circumferential clearances so that to avoid "trigger" motions during the reversing of the rotation direction of the motor output shaft 17.

The elastic means 18 comprise a preferably coil spring concentrically mounted on the motor output shaft 17 and interposed between the second clutch 8 and the supporting element 22 to apply a thrust longitudinally onto the second clutch 8.

During the assembling of the device 1, the elastic means 18 push the second clutch 8 towards the first clutch 7, to allow the mutual coupling between the teeth 14 and the seats 15 of the first clutch 7 and the teeth and the seats of the third clutch 41 between the teeth and the seats 1 of the fourth clutch 42 and the teeth and the seats of the second clutch 8.

If there is not a perfect coupling between the teeth and the seat of the reciprocal clutches, when the motor 19 is activated, the second clutch tends to move in the longitudinal direction towards the proximal portion of the handpiece 2 and to come back immediately towards the distal direction, pushed by the elastic means 8, until the coupling between the teeth and the seats of the reciprocal clutches is not reached.

The afore said operation requires only split seconds and is as quicker as the number of teeth and seats of clutches 7, 8, 41, 42 increases.

To stop the sliding in the longitudinal direction of the second clutch 8, a limit element 25 is present along the motor output shaft 17.

The limit element 25, represented by a seeger circlip, is mounted at the end of the motor output shaft 17, distally from the second clutch 8.

In FIG. 4 two conical protecting elements 53, 54 are further shown, preferably made of aluminium.

In detail, the conical ring 54 is mounted on the body 40 and the conical ring 53 is screwed on the conical ring 54 through a not shown thread.

The conical rings 53, 54 protect the clutch from the outside and avoid everyone from incidentally reaches the clutch 8 during its operation.

Preferably, a second sealing element 55 is provided on the conical ring 53 in its appropriate groove, such as a rubber O-ring, to protect the guiding means 5 from the contamination of sucked liquids, in case the first sealing element 34 should break.

Preferably, the device 1 according to the present invention comprises a sucking and cooling circuit comprising a connection 9 for a sucking apparatus, outside of the handpiece 2 and not shown in figures, at least one duct directing the cooling fluid from said connection 9 to the inner tubular element 4 and a device for adjusting the cooling fluid feed to the inner tubular element.

According to an advantageous aspect of the present invention, the handpiece 2 is sealed.

The present invention has been described referring to some embodiments. To the embodiments herein represented in detail may be made various modifications, anyway remaining in the protection scope of the invention, defined by the following claims.

The invention claimed is:

1. A device for treatments of endoscopic resection comprising:
   a handpiece adapted to be grasped by a user;
   an outer tubular element extending along a longitudinal axis (X-X) comprising a proximal end, a distal end and a cutting opening arranged at said distal end;
   an inner tubular element adapted to be rotatably accommodated in said outer tubular element; said inner tubular element extending along a longitudinal axis (X-X) and comprising a proximal end, a distal end and a cutting tip at its distal end;
   guiding means for rotating and/or oscillating said inner tubular element with respect to said outer tubular element; said guiding means comprising an i) electric motor with a motor output shaft with a distal end and ii) at least one power-supply battery pack for said electric motor; contained inside said handpiece;
   a first clutch keyed on the inner tubular element substantially at the proximal end of the inner tubular element so that said inner tubular element can be removed from the handpiece;
   a motor output shaft;
   a second clutch keyed on the distal end of the motor output shaft and thereby axially slidable on the motor output shaft so that to axially slide on the motor output shaft;
   a motion transmitting member, interposed between said first clutch and said second clutch for decoupling the first clutch from said second clutch;
   said second clutch being shaped for coupling with said transmitting member;
   and said first clutch being shaped for removably coupling with said transmitting member;
   a supporting element fixedly-keyed through a fastening means to said motor output shaft while the second clutch is slidable along said motor output shaft; said supporting element being adapted to make said second clutch rotate.

2. The device according to claim 1, wherein said transmitting member comprises:
   a third clutch adapted for coupling with said first clutch;
   a fourth clutch adapted for coupling with said second clutch; and
   at least one sealing element extending radially in order to avoid a fluid passage to said guiding means.

3. The device according to claim 1, wherein said first clutch comprises a first crown wheel comprising a plurality of teeth spaced along a circumference to form a plurality of seats and in that said third clutch comprises a third crown wheel comprising a plurality of teeth spaced along a circumference to form a plurality of seats.

4. The device according to claim 1, wherein,
   said fourth clutch comprises a fourth crown wheel comprising a plurality of teeth spaced along a circumference to form a plurality of seats, and
   said second clutch comprises a crown wheel comprising a plurality of teeth spaced along a circumference and adapted to engage the seats of said fourth crown wheel of said fourth clutch.

5. The device according to claim 2, wherein said transmitting member further comprises at least one centering element extending around a central axis X-X of the transmitting member itself to axially align said first clutch with the third clutch and the second clutch with said fourth clutch.

6. The device according to claim 1, further comprising a fastening member for radially constraining said transmitting member to said handpiece.

7. The device according to claim 2, wherein said third clutch and said fourth clutch are disjointly made.

8. The device according to claim 5, wherein said transmitting member comprises an abutment element for said sealing element comprising a disc-shaped element that radially extends around the central axis X-X from said second clutch.

9. The device according to claim 1, further comprising at least one elastic element in order to push said second clutch to couple with the fourth clutch and said third clutch to couple with the first clutch.

10. The device according to claim 9, wherein said at least one elastic element comprise a spring concentrically mounted on the motor output shaft and interposed between said second clutch and said supporting element to apply a thrust longitudinally onto said second clutch.

11. The device according to claim 1, further comprising a limit element of the longitudinal sliding of said second clutch, said limit element being mounted on the end of said motor output shaft distally from said second clutch.

12. The device according to claim 1, wherein said electric motor and said at least one power-supply battery pack are contained in at least one closed body, the at least one closed body being contained and removably fastened in the handpiece.

13. The device according to claim 2, wherein said first clutch comprises a first crown wheel comprising a plurality of teeth spaced along a circumference to form a plurality of seats and in that said third clutch comprises a third crown wheel comprising a plurality of teeth spaced along a circumference to form a plurality of seats.

14. The device according to claim 2, wherein said second clutch comprises a crown wheel comprising a plurality of teeth spaced along a circumference and adapted to engage the seats of said first crown wheel and in that said fourth clutch comprises a fourth crown wheel comprising a plurality of teeth spaced along a circumference to form a plurality of seats.

15. The device according to claim 3, wherein said second clutch comprises a crown wheel comprising a plurality of teeth spaced along a circumference and adapted to engage the seats of said first crown wheel and in that said fourth clutch comprises a fourth crown wheel comprising a plurality of teeth spaced along a circumference to form a plurality of seats.

16. The device according to claim 3, wherein said transmitting member further comprises at least one centering element extending around a central axis X-X of the transmitting member itself to axially align said first clutch with the third clutch and the second clutch with said fourth clutch.

17. The device according to claim 4, wherein said transmitting member further comprises at least one centering element extending around a central axis X-X of the transmitting member itself to axially align said first clutch with the third clutch and the second clutch with said fourth clutch.

18. The device according to claim 2, further comprising a fastening member for radially constraining said transmitting member to said handpiece.

19. The device according to claim 3, wherein said third clutch and said fourth clutch are disjointly made and comprise removable fastening means to make them integral.

20. A device for treatments of endoscopic resection comprising:
a handpiece adapted to be grasped by a user; an outer tubular element extending along a longitudinal axis (X-X) comprising a proximal end, a distal end and a cutting opening arranged at said distal end;
an inner tubular element adapted to be rotatably accommodated in said outer tubular element; said inner tubular element extending along a longitudinal axis (X-X) and comprising a proximal end, a distal end and a cutting tip at its distal end;
guiding means for rotating and/or oscillating said inner tubular element with respect to said outer tubular element; said guiding means comprising an i) electric motor with a motor output shaft with a distal end and ii) at least one power-supply battery pack for said electric motor contained inside said handpiece;
a first clutch keyed on the inner tubular element substantially at the proximal end of the inner tubular element so that said inner tubular element can be removed from the handpiece;
a motor output shaft;
a second clutch keyed on the distal end of the motor output shaft and thereby axially slidable on the motor output shaft so that to axially slide on the motor output shaft;
a motion transmitting member, interposed between said first clutch and said second clutch for decoupling the first clutch from said second clutch;
said second clutch being shaped for coupling with said transmitting member;
and said first clutch being shaped for removably coupling with said transmitting member;
a supporting element fixedly-keyed through the fastening means to said motor output shaft, said supporting element being adapted to make said second clutch rotate; and
at least one elastic element comprising a spring concentrically mounted on the motor output shaft and interposed between said second clutch and the supporting element to apply a thrust longitudinally onto second clutch.

21. The device according to claim 20, wherein said transmitting member comprises:
a third clutch adapted for coupling with said first clutch;
a fourth clutch adapted for coupling with said second clutch; and
at least one sealing element extending radially in order to avoid a fluid passage to said guiding means.

22. The device according to claim 20, wherein said spring is concentrically mounted surrounding the motor output shaft.

23. The device according to claim 20, wherein said inner tubular element has its distalmost end completely inside and surrounded by said outer tubular element.

24. The device according to claim 1, wherein said inner tubular element has its distalmost end completely inside and surrounded by said outer tubular element.

* * * * *